(12) United States Patent
Chatterji

(10) Patent No.: US 8,936,817 B2
(45) Date of Patent: Jan. 20, 2015

(54) PREPARATION FOR WEIGHT LOSS MANAGEMENT

(75) Inventor: Arun K. Chatterji, Neenah, WI (US)

(73) Assignee: Ayurvedic-Life International, LLC, Neenah, WI (US)

( * ) Notice: Subject to any disclaimer, the term of this patent is extended or adjusted under 35 U.S.C. 154(b) by 81 days.

(21) Appl. No.: 13/695,573

(22) PCT Filed: May 3, 2011

(86) PCT No.: PCT/US2011/000767
§ 371 (c)(1),
(2), (4) Date: Jan. 7, 2013

(87) PCT Pub. No.: WO2011/139354
PCT Pub. Date: Nov. 10, 2011

(65) Prior Publication Data
US 2013/0136814 A1 May 30, 2013

Related U.S. Application Data

(60) Provisional application No. 61/343,879, filed on May 5, 2010.

(51) Int. Cl.
| | |
|---|---|
| *A61K 36/324* | (2006.01) |
| *A61K 36/27* | (2006.01) |
| *A61K 36/328* | (2006.01) |
| *A61K 36/59* | (2006.01) |
| *A61K 36/32* | (2006.01) |

(52) U.S. Cl.
CPC ............... *A61K 36/324* (2013.01); *A61K 36/27* (2013.01); *A61K 36/328* (2013.01); *A61K 36/59* (2013.01); *A61K 36/32* (2013.01)
USPC ........................... 424/748; 424/774; 424/779

(58) Field of Classification Search
CPC ... A61K 36/324; A61K 36/328; A61K 36/59; A61K 36/27
USPC ......................................... 424/774, 779, 748
See application file for complete search history.

(56) References Cited

U.S. PATENT DOCUMENTS

| | | | | |
|---|---|---|---|---|
| 5,886,029 | A * | 3/1999 | Dhaliwal | 514/456 |
| 8,541,383 | B2 * | 9/2013 | Gokaraju et al. | 514/27 |
| 2003/0004215 | A1 * | 1/2003 | Van Laere et al. | 514/557 |

FOREIGN PATENT DOCUMENTS

JP 11137211 A * 5/1999

OTHER PUBLICATIONS

Kar (Journal of Ethnopharmacology (2003), vol. 83, pp. 105-108).*

* cited by examiner

*Primary Examiner* — Susan Hoffman
(74) *Attorney, Agent, or Firm* — Olson & Cepuritis, Ltd.

(57) ABSTRACT

*Gymnema sylvestre* extracts together with extracts of one or more of *Boswellia serrata, Tinospora cordifolia* and *Commiphora mukul* provide effective weight loss management when administered to a patient desiring weight loss management. Administration of the foregoing also reduces the leptin-to-adiponectin ratio in the patient's blood serum.

9 Claims, No Drawings

PREPARATION FOR WEIGHT LOSS MANAGEMENT

CROSS-REFERENCE TO RELATED APPLICATIONS

This application is a U.S. National Stage of PCT/US2011/000767, filed May 3, 2011, and claims benefit of U.S. Provisional Patent Application No. 61/343,879, filed May 5, 2010, each of which is incorporated herein by reference in its entirety.

FIELD OF INVENTION

This invention relates to weight loss management and compositions therefor.

BACKGROUND OF INVENTION

A relatively high percentage of U.S. population is overweight, that is, exhibiting a basic metabolic index or body mass index (BMI) greater than 25, and one quarter of the U.S. population is obese, exhibiting a BMI greater than 30. Annually, a large number of deaths can be attributed to obesity. Therefore, a healthy weight maintenance requires a balance between energy intake and energy output for an individual.

Adipose derived hormones such as adiponectin and leptin are secreted by adipose tissue and control various physiological systems in a mammalian body. Low leptin levels, for example, stimulate food intake, reduce energy expenditure, and modulate neuroendocrine and immune functions to conserve energy stores. While normally leptin is a signal that reduces appetite, it is known that obese persons have an unusually high circulating concentration of leptin and may be resistant to the usual effects of leptin in a manner similar to patients suffering from Type 2 diabetes that are resistant to the effects of insulin. High sustained concentrations of leptin may result in undesirable leptin desensitization or leptin resistance.

Adiponectin is produced by adipocytes in adipose tissue and is secreted into the bloodstream. Levels of adiponectin in the bloodstream are inversely correlated with body fat percentage in adults. It is believed that adiponectin plays a role in the suppression of metabolic events that may result in Type 2 diabetes and obesity.

SUMMARY OF THE INVENTION

The present invention is directed to compositions that reduce the leptin-to-adiponectin ratio in overweight patients and promote weight loss.

The compositions comprise a solid, ethanolic extract derived from *Gymnema sylvestre* leaves which contains no more than about 55 weight percent of a gymnemic acid and one or more of (1) a solid, ethanolic extract from *Boswellia serrata* gum containing at lest 70 weight percent boswellic acids, (2) a solid, ethanolic extract from the stems of *Tinospora cordifolia*, and (3) a solid, ethanolic extract from *Commiphora mukul* gum.

The daily dosage for a patient desiring weight management preferably is about 500 milligrams to about 1,000 milligrams of the composition or the components thereof administered substantially concurrently.

DESCRIPTION OF PREFERRED EMBODIMENTS

The present compositions include an ethanolic extract from *Gymnema sylvestre* leaves in powder form. This ethanolic extract is constituted by about 25 to about 55 weight percent of gymnemic acids, but may also contain gymnemasaponins. There are 18 known gymnemic acids, i.e., gymnemic acids I-XVIII, and the term "gymnemic acid" as used herein includes one or more of the aforementioned gymnemic acids which may or may not be acylated. Particularly desirable for the present compositions are gymnemic acids III, IV, V and VII.

A preferred solid, ethanolic extract from *Gymnema sylvestre* is prepared as set forth below.

(1) *Gymnema sylvestre* leaves are sourced and checked for their botanical purity. The leaves are then disintegrated (powdering the leaves into smaller size using a pulveriser) to a size passing through a 20 Mesh sieve, U.S. Standard Sieve Series.

(2) Obtained powder is then extracted with 50% v/v ethanol and demineralized water (solvent). 40 grams of powdered leaves are held in 1 liter of solvent at room temperature overnight-up to 12 hours in a shaker, distributed in four Erlenmeyer flasks. The contents are then pooled and filtered.

(3) The obtained micelle is concentrated under reduced pressure (650-700 mm) to 30% solids at pH of less than or equal to 2.

(4) The concentrate from above is dissolved in 1 liter of demineralized water at room temperature, in a shaker for 4 hours while adjusting the final pH to about 4.5 to about 5, and filtered to remove any precipitate and sludge.

(5) The obtained filtrate is adjusted to a pH of about 2 and filtered to remove any precipitate and sludge.

(6) The new filtrate is concentrated under reduced pressure (650-700 mm) to 30% solids, and sterilized (Heat Sterilization) at about 80° C. for 2 hours.

(7) The product is adjusted for at least 25 but no more than 55% by weight gymnemic acid, preferably about 35 to about 45 weight percent gymnemic acid.

(8) The product is then dried in spray dryer at inlet temp of 160° C. and outlet temp of 85° C.

(9) The dried product is checked for gymnemic acid content.

(10) The powder is homogenized and sifted to 80-100 Mesh, U.S. Standard Sieve Series.

The solid, ethanolic extract from *Boswellia serrata* gum is rich in boswellic acids, particularly the alpha, beta, and gamma boswellic acids. These acids comprise a pentacyclic triterpene, a carboxyl group, and at least one other functional group which can be a hydroxyl group, an acetyl group or a keto group.

A preferred solid, ethanolic extract from *Boswellia serrata* gum is prepared as set forth below.

(1) The boswellia gum exudate is cleaned by removing bark and foreign organic matter adhering to the exudate.

(2) The exudate is then extracted with ethanol.

(3) The ethanol is then partially distilled from the obtained micella which is adjusted to a slightly alkaline pH.

(4) The obtained gum product is then extracted with petroleum ether and ethanol in a liquid-liquid extractor at ambient temperature.

(5) The obtained liquid phases are separated and processed separately.

(6) The petroleum ether fraction affords an aromatic fraction mainly composed of essential oil and resinous matter. The recovery is done by distillation. This matter is removed.

(7) The ethanolic fraction is further processed by heating under vacuum to remove residual petroleum ether.

(8) The processed ethanolic fraction is concentrated to 30-35% solids and poured under vigorous stirring into demineralized water to produce a boswellic acid precipitate which is recovered.
(9) The precipitate is washed with 80/20 v/v ethanol and ethyl acetate mixture to remove any unwanted fractions of boswellic acid until 70% boswellic acid by weight is achieved with only an alpha, beta, and gamma boswellic acid present.
(10) The aqueous phase is decanted off. Precipitate is washed further with demineralized water, and dried under vacuum at a temperature of about 60° C.
(11) The dried flakes obtained are pulverized, and contain at least 70% by weight of boswellic acids.

The solid, ethanolic extract from the stems of *Tinospora cordifolia* contains diterpenes such as tinosporaside, cordiofolide, cordifol, heptacosanol, clerodane furano diterpene, diterpenoid furanolactone tinosporidine, columbin and beta-sitosterol.

A preferred solid, ethanolic extract can be prepared as shown below.
(1) Well matured *Tinospora cordifolia* stems, ⅜" to ½" diameter and 3" to 5" in length, with the outside bark color of dark brown having irregular thin red lines, are washed with water and dried in cool shade, and then crushed in a disintegrator into coarse chunks, from which the bark pieces are removed.
(2) The coarse chunks of the stems are pulverized and the remainder of the bark is separated therefrom. The inner body of the stems, having light beige to light brown color, constitute the starting powder material ("core") which is then treated further.
(3) 200 Grams of the "core" powder material are then extracted with two liters of 50% v/v ethanol followed by demineralized water.
(4) The extracted solutions received from the foregoing hydro-alcoholic and aqueous extractions are concentrated separately, and then mixed in a homogenizer to make a homogenous solution before final concentration.
(5) The concentration is done under controlled temperature at pH of less than about 4 for about two hours.
(6) When a concentration of 30-35% solids is achieved, the material can be spray dried, or it can be further concentrated to a thick paste of 65-70% solids.
(7) The concentrate or the thick paste are then dried in vacuum tray dryer or rotary vacuum dryer at a temperature not to exceed about 65° C.
(8) The obtained dried flakes are pulverized to 80-100 Mesh, U.S. Sieve Series, and packed under hygienic conditions.
(9) Before packing the powder can be sterilized, if desired, by passing through a hot duct maintained at a temperature of 120° C.

The solid, ethanolic extract from *Commiphora mukul* gum contains guggalsterone, also known as guggal lipid.

A preferred extract can be prepared as shown below.
(1) The *Commiphora mukul* gum is first checked for purity by TLC, and subjected to a four step grading process.
(2) 200 Grams of selected, crushed gum is then loaded into an extractor and ethanol, about five times the weight of gum with water (50/50) is charged through the extractor.
(3) In the extractor the temperature is kept between 65-70° C. and the ethanol-water is circulated under turbulence conditions for through mixing and efficient extraction.
(4) Extracted mucilage is then taken to a falling film evaporator for solvent recovery.
(5) The obtained guggal paste is then enriched in guggalsterones by solvent fractionation.
(6) The enriched paste obtained in this manner is then kept under vacuum for solvent removal.
(7) The product is then dried in a fluid bed dryer.
(8) The dried product is sieved and again tested for guggalsterone content.

The present invention is illustrated by the following examples.

Example 1

Weight Reduction Using Enhanced *G. sylvestre* Extract

Obese volunteers (n=10; 6 male, 4 female), marginally diabetic and about 20 percent overweight patients, were treated with a solid, ethanolic extract of *G. sylvestre* or a solid, ethanolic extract of *G. sylvestre* enhanced by the addition of an amount of a solid, steranolic extract of *B. serrata* in an amount sufficient to provide a boswellic acid content of about 3.5 percent by weight of the total composition.

The patients exhibited a fasting blood sugar level (FBS) of 130-140 milligrams per deciliter (mg/dl). The average age of the patient group was 35-45 years.

The composition was administered orally in a capsule form. Each capsule contained 250 milligrams of the composition. One or more capsules were administered to obtain the desired dosage.

Physical parameters and blood chemistry were monitored. Serum leptin and adiponectin were determined using an ELISA kit (R&D System, Inc., Minneapolis, Minn., U.S.A.).

TABLE I

Physical Parameters (Average Values)

| | | % decrease - after 60 days | | | | | |
|---|---|---|---|---|---|---|---|
| Dosage | Sex | Body wt. (Kg) | Chest (cm) | Waist (cm) | Hip (cm) | W/H Ratio | BMI |
| 500 mg | Male | (−) 3.00 | No Change | (−) 1.18 | (−) 0.35 | (−) 3.37 | (−) 2.09 |
| 60 days | Female | (−) 2.10 | (−) 0.125 | (−) 1.02 | (−) 0.26 | (−) 3.92 | (−) 1.44 |
| 1000 mg | Male | (−) 2.70 | (−) 0.80 | (−) 2.12 | (−) 1.25 | (−) 1.94 | (−) 2.51 |
| 60 days | Female | (−) 4.24 | (−) 0.63 | (−) 1.25 | (−) 0.50 | (−) 2.35 | (−) 2.35 |
| W/O | Male | (−) 3.10 | No Change | (−) 1.19 | (−) 0.36 | (−) 3.30 | (−) 2.08 |

W/H—waist-to-hip ratio
BMI—basic metabolic index (body mass index)
W/O—*G. sylvestre* extract without added enhancer

TABLE II

Blood Chemistry Improvements (Average Values)

| | | % decrease - after 60 days | | | | |
|---|---|---|---|---|---|---|
| Dosage | Sex | FBS | TGL | CHOL | HDL | LDL |
| 500 mg | Male | (−) 11.50 | (−) 6.00 | (−) 6.00 | (+) 6.50 | (−) 2.80 |
| 60 days | Female | (−) 17.50 | (−) 14.50 | (−) 6.00 | (+) 4.50 | (−) 3.50 |
| 1000 mg | Male | (−) 14.61 | (−) 14.61 | (−) 6.50 | (+) 18.00 | (−) 11.16 |
| 60 days | Female | (−) 19.50 | (−) 6.25 | (−) 14.00 | (+) 8.00 | (−) 14.50 |
| W/O | Male | (−) 11.62 | (−) 6.10 | (−) 6.15 | (+) 6.60 | (−) 2.78 |

FBS—fasting blood sugar, mg/dl
TGL—triglycerides
CHOL—Cholesterol
HDL—high density lipoprotein
LDL—low density lipoprotein
W/O—*G. sylvestre* extract without added enhancer

TABLE III

Leptin and Adiponectin Concentration After 60 Days at 500 mg/day

| Sex | Code Name | Leptin (picogram/ml) | | | Adiponectin (nanogram/ml) | | | L/A (BT) | L/A (AT) |
|---|---|---|---|---|---|---|---|---|---|
| | | BT | AT | % decrease (−) | BT | AT | % increase (+) | | |
| MALE | DS | 4987 | 4388 | −13% | 879 | 975 | +11% | 5.67 | 4.50 |
| | TH | 4498 | 3868 | −8% | 2129 | 2320 | +9% | 2.11 | 1.67 |
| | NB | 5237 | 4294 | −18% | 3267 | 3659 | +12% | 1.60 | 1.17 |
| | PB | 3847 | 3269 | −15% | 6981 | 7609 | +9% | 0.55 | 0.42 |
| | SH | 4428 | 3810 | −14% | 5390 | 5929 | +13% | 0.82 | 0.64 |
| | SM | 4611 | 4252 | −8% | 1400 | 1568 | +12% | 3.29 | 2.71 |
| FEMALE | GP | 3911 | 3324 | −15% | 5742 | 6316 | +10% | 0.68 | 0.53 |
| | DH | 3787 | 3181 | −17% | 1059 | 1165 | +10% | 3.57 | 2.73 |
| | UC | 4498 | 3643 | −18% | 1456 | 1630 | +12% | 3.08 | 2.23 |
| | TS | 3618 | 3003 | −17% | 4488 | 5929 | +13 | 0.81 | 0.50 |

BT—before treatment
AT—after treatment
L/A (BT)—leptin-to-adiponectin ratio before treatment
L/A (AT)—leptin-to-adiponectin ratio after treatment

TABLE IV

Leptin and Adiponectin Concentration After 60 Days at 1000 mg/day

| Sex | Code Name | Leptin (picogram/ml) | | | Adiponectin (nanogram/ml) | | | L/A (BT) | L/A (AT) |
|---|---|---|---|---|---|---|---|---|---|
| | | BT | AT | % decrease (−) | BT | AT | % increase (+) | | |
| Male | AG2 | 4498 | 3643 | −19% | 911 | 1056 | +16% | 4.94 | 3.45 |
| | UM | 5237 | 4032 | −23% | 7313 | 8409 | +15% | 0.72 | 0.48 |
| | GR | 4264 | 3112 | −27% | 2543 | 2975 | +17% | 1.68 | 1.05 |
| | AG | 4264 | 3411 | −20% | 5265 | 5844 | +11% | 0.81 | 0.58 |
| | AS | 5012 | 3362 | −33% | 2666 | 3441 | +29% | 1.88 | 0.98 |
| | DC | 4672 | 3504 | −25% | 1994 | 2392 | +20% | 2.34 | 1.20 |
| Female | GK | 3632 | 2978 | −18% | 8923 | 10439 | +17% | 0.41 | 0.29 |
| | SM | 3798 | 2772 | −27% | 1145 | 1385 | +21% | 3.32 | 2.00 |
| | UH | 3911 | 2463 | −37% | 1783 | 2175 | +22% | 2.19 | 1.13 |
| | AM | 4108 | 3286 | −20% | 3612 | 4478 | +24% | 1.14 | 0.73 |

BT—before treatment
AT—after treatment

The foregoing results indicate the achievement of reduced fasting blood sugar level as well as an improved lipid profile and a decrease in the leptin-to-adiponectin ratio for each patient.

Example 2

Effect of Enhancers on *G. sylvestre* Efficacy

Capsules containing solid, ethanolic extract of *G. sylvestre* were prepared as well as capsules containing solid, ethanolic extracts of *Tinospora cordifolia* and *Commiphora mukul*. Predetermined dosages of the *G. sylvestre* extract alone or together with the extract of *T. codifolia* or *C. mukul* were administered to volunteer male patients which were marginally diabetic, exhibiting a fasting blood sugar level of 125-135 mg/dl, and about 20 percent overweight. The average age of the patient group was 30-45 years.

The patient's physical parameters, levels of changes in fasting blood sugar, blood cholesterol, high density lipoprotein, low density lipoprotein, as well as triglyceride were determined. Leptin and adiponectin concentrations were measured. The results are reported below.

TABLE V

Effects on Obesity Achieved by *G. sylvestre* Extract with Enhancers

| | % decrease - after 60 days | | | | | |
|---|---|---|---|---|---|---|
| Extract Dosage | Body wt. (Kg) | Chest (Cm) | Waist (Cm) | Hip (Cm) | W/H ratio | BMI |
| 500 mg *G. sylvestre* | (−) 3.10 | No change | (−) 1.19 | (−) 0.36 | (−) 3.30 | (−) 2.08 |
| 250 mg *G. sylvestre* 250 mg. *T. cordifolia* | (−) 2.90 | No change | (−) 1.28 | (−) 0.36 | (−) 3.55 | (−) 2.10 |
| 250 mg *G. sylvestre* 250 mg *G. mukul* | (−) 3.10 | No change | (−) 2.00 | (−) 0.48 | (−) 4.16 | (−) 2.21 |

W/H ratio—waist-to-hip ratio
BMI—basic metabolic index (body mass index)

TABLE VI

Effects on Blood Chemistry Achieved by *G. sylvestre* Extract with Enhancers

| | % decrease - after 60 days | | | | |
|---|---|---|---|---|---|
| Extract Dosage | FBS | TGL | CHOL | HDL | LDL |
| 500 mg *G. sylvestre* | (−) 11.62 | (−) 6.10 | (−) 6.15 | (+) 6.60 | (−) 2.78 |
| 250 mg *G. sylvestre* 250 mg *T. cordifolia* | (−) 12.20 | (−) 8.00 | (−) 4.50 | (+) 2.80 | (−) 3.00 |
| 250 mg *G. sylvestre* 250 mg *C. mukul* | (−) 13.00 | (−) 7.06 | (−) 5.50 | (+) 4.80 | (−) 2.60 |

FBS—fasting blood sugar, mg/dl
TGL—triglycerides
CHOL—cholesterol
HDL—high density lipoprotein
LDL—low density lipoprotein The data shown in Tables V and VI show a beneficial decrease in the serum levels of fasting blood sugar, triglycerides, cholesterol and low density lipoproteins but a beneficial increase in high density lipoprotein level.

TABLE VII

Decrease in Leptin-to-Adiponectin Ratio in Male Patients

| | | Leptin (picogram/ml) | | | Adiponectin (nanogram/ml) | | | | |
|---|---|---|---|---|---|---|---|---|---|
| Dosage | Code | BT | AT | % decrease (−) | BT | AT | % increase (+) | L/A (BT) | L/A (AT) |
| 500 mg *G. sylvestre* | SG | 3925 | 3780 | −3.69% | 1020 | 1110 | +8.82% | 3.89 | 3.41 |
| | TL | 4045 | 3850 | −4.82% | 2215 | 2420 | +9.25% | 1.83 | 1.59 |
| | SK | 4126 | 3910 | −5.23% | 2890 | 3120 | +7.95% | 1.43 | 1.25 |
| | AB | 3950 | 3170 | −19.74% | 4950 | 5200 | 5.05% | 0.80 | 0.61 |
| | SD | 4880 | 4218 | −13.56% | 4612 | 4950 | +7.32% | 1.06 | 0.85 |
| | BP | 4666 | 4155 | −10.95% | 1680 | 1920 | +14.28% | 2.78 | 2.16 |

TABLE VII-continued

Decrease in Leptin-to-Adiponectin Ratio in Male Patients

| Dosage | Code | Leptin (picogram/ml) | | | Adiponectin (nanogram/ml) | | | L/A (BT) | L/A (AT) |
|---|---|---|---|---|---|---|---|---|---|
| | | BT | AT | % decrease (−) | BT | AT | % increase (+) | | |
| 250 mg | MP | 3980 | 3660 | −8.04% | 2566 | 3100 | +20.80% | 1.55 | 1.18 |
| *G. sylvestre* | BG | 4610 | 4120 | −10.62% | 1880 | 2106 | +12.02% | 2.45 | 1.96 |
| 250 mg | PG | 4235 | 3980 | −6.02% | 1200 | 1300 | +8.33% | 3.53 | 3.06 |
| *T. cordifolia* | TS | 5432 | 4880 | −10.16% | 2681 | 2920 | +8.91% | 2.03 | 1.67 |
| | MM | 3656 | 3200 | −12.47% | 4880 | 5200 | +6.55% | 0.73 | 0.61 |
| | KC | 3980 | 3650 | −8.29% | 5415 | 5820 | +7.47% | 0.73 | 0.63 |
| 250 mg | KM | 4220 | 3660 | −13.27% | 1120 | 1310 | +16.96% | 3.77 | 2.79 |
| *G. sylvestra* | BS | 3568 | 2900 | −8.72% | 6520 | 6800 | +4.27% | 0.55 | 0.43 |
| 250 mg | ST | 4164 | 3020 | −27.47% | 2646 | 3100 | +17.15% | 1.57 | 0.97 |
| *C. mukul* | SP | 5015 | 3960 | −21.03% | 5210 | 5920 | +13.62% | 0.96 | 0.67 |
| | NS | 4522 | 3880 | −14.19% | 2800 | 3460 | +23.57% | 1.61 | 1.12 |
| | PB | 3156 | 2220 | −29.65% | 2222 | 2480 | +11.61% | 1.42 | 0.90 |

BT—before treatment
AT—after treatment
L/A (BT)—leptin-to-adiponectin ratio before treatment
L/A (AT)—leptin-to-adiponectin ratio after treatment Data in Table VII show a consistent decrease in the leptin-to-adiponectin ratio for all patients.

The foregoing discussion and the Examples are intended to be illustrative but are not to be taken as limiting. Still other variants within the spirit and scope of the present invention are possible and will readily present themselves to those skilled in the art.

The invention claimed is:

1. An oral composition consisting essentially of solid, ethanolic extract from *Gymnema sylvestre* leaves containing about 25 to about 55 weight percent gymnemic acid and an enhancer which is a member of the group consisting of a solid, ethanolic extract from *Boswellia serrata* gum containing at least 70 weight percent boswellic acids, a solid ethanolic extract from the stems of *Tinospora cordifolia*, a solid ethanolic extract from *Commiphora mukul* gum, and mixtures thereof.

2. The oral composition in accordance with claim 1 wherein the solid, ethanolic extract from *Boswellia serrata* gum is present in an amount of at least 3 percent by weight, based on the weight of the solid, ethanolic extract from *Gymnema sylvestre* leaves.

3. The oral composition in accordance with claim 1 wherein said enhancer is a solid ethanolic extract from the stems of *Tinospora cordifolia*.

4. The oral composition in accordance with claim 1 wherein said enhancer is a solid, ethanolic extract from *Commiphora mukul* gum.

5. The oral composition of claim 1 consisting essentially of said *Gymnema sylvestre* extract, said *Boswellia serrata* extract and at least one of said *Tinospora cordifolia* extract and said *Commiphora mukul* extract.

6. A method for reducing leptin-to-adiponectin ratio in serum of a patient which comprises administering to the patient the composition of claim 1.

7. A method for reducing leptin-to-adiponectin ratio in serum of a patient which comprises administering to the patient the composition of claim 2.

8. A method for reducing leptin-to-adiponectin ratio in serum of a patient which comprises administering to the patient the composition of claim 3.

9. A method for reducing leptin-to-adiponectin ratio in serum of a patient which comprises administering to the patient the composition of claim 4.

* * * * *